United States Patent [19]

Albrecht et al.

[11] 4,348,334

[45] Sep. 7, 1982

[54] PROCESS FOR PRODUCING THE MAGNESIUM SALT OF 3-NITRO-NAPHTHALENE-1,5-DISULFONIC ACID (NITRO-ARMSTRONG'S ACID)

[75] Inventors: Bernhard Albrecht, Buus; Hans Frey, Bettingen; Vinzenz Habermacher, Basel, all of Switzerland; Horst Behre, Odenthal, Fed. Rep. of Germany; Lutz Kienitz, Bergisch Gladbach, Fed. Rep. of Germany; Wolfgang Schenk, Leverkusen, Fed. Rep. of Germany; Guido Steffan; Axel Vogel, both of Odenthal, Fed. Rep. of Germany

[73] Assignees: Ciba-Geigy AG, Basel, Switzerland; Bayer Aktiengesellschaft, Leverkusen, Fed. Rep. of Germany

[21] Appl. No.: 113,412

[22] Filed: Jan. 18, 1980

[30] Foreign Application Priority Data

Feb. 2, 1979 [CH] Switzerland ............... 1045/79

[51] Int. Cl.$^3$ .............................. C07C 143/55
[52] U.S. Cl. ................................. 260/505 C
[58] Field of Search ..................... 260/505 C

[56] References Cited

U.S. PATENT DOCUMENTS 1,756,537  4/1930  Cotton ............................ 260/505 C
2,191,820  2/1940  Berretta ......................... 260/505 C

OTHER PUBLICATIONS

Gilbert, "Sulfonation and Related Reactions", pp. 2–6, (1965).
Roberts, "Modern Experimental Chemistry", pp. 35–39 (1969).

*Primary Examiner*—Michael L. Shippen

*Attorney, Agent, or Firm*—Joseph G. Kolodny

[57] ABSTRACT

A process for producing the magnesium salt of 3-nitro-naphthalene-1,5-disulfonic acid by sulfonating naphthalene, nitrating the sulfonation product, and separating the pure magnesium salt of 3-nitronaphthalene-1,5-disulfonic acid, which process comprises:

(a) sulfonating naphthalene with liquid $SO_3$ in the presence of an inert organic solvent at temperatures between $-40°$ and $+20°$ C.;

(b) adding to the reaction mixture obtained a mixture consisting of about equal parts of 100% sulfuric acid and fully reacted crude nitration mixture from nitration of a previous nitration charge, separating from the resulting two-phase system the upper organic solvent phase by decanting, and removing from the Armstrong's acid anhydride acid slurry the remainder of organic solvent by distillation, or removing it during or after subsequent nitration, subsequently adding to the residue the amount of nitric acid required for nitration, and then nitrating;

(c) adding then firstly water and afterwards, in the absence of the inert organic solvent, at 90° to 120° C., a compound releasing magnesium ions, the amount being such that, per mol of 3-nitronaphthalene-1,5-disulfonic acid, 1.1 to 1.3 mols of magnesium ions are added, and a sulfuric acid concentration of between 40 and 60 percent by weight (relative to the sulfuric acid and water) is maintained; and (d) separating the crystallized magnesium salt of 3-nitronaphthalene-1,5-disulfonic acid at a temperature of between 20° and 70° C., and subsequently optionally washing it with a maximum of 60 percent by weight of sulfuric acid and/or water, and optionally drying the product.

16 Claims, No Drawings

PROCESS FOR PRODUCING THE MAGNESIUM SALT OF 3-NITRO-NAPHTHALENE-1,5-DISULFONIC ACID (NITRO-ARMSTRONG'S ACID)

The present invention relates to a process for producing the magnesium salt of 3-nitronaphthalene-1,5-disulfonic acid (nitro-Armstrong's acid, referred to hereinafter as nitro-AA) by nitrating a product mixture which has been obtained by reaction of naphthalene with sulfur trioxide in an inert organic solvent; and adding to the nitration mixture, which has been diluted with water, a compound releasing magnesium ions.

It is known from the U.S. Pat. No. 2,191,820 that nitro-AA can be produced by firstly introducing pure naphthalene-1,5-disulfonic acid and 60% oleum, below 40° C., into sulfuric acid monohydrate (100% $H_2SO_4$); slowly adding to this mixture, below 30° C., an anhydrous mixture of sulfuric acid and nitric acid ($HNO_3$ content=40%); and stirring for 6 to 7 hours at 30° to 35° C. The nitration mixture is subsequently diluted with water and, after the addition of magnesium oxide, the nitro-AA is isolated as magnesium salt. This process necessitates the involved process of isolating pure naphthalene-1,5-disulfonic acid.

A process has nown been found for producing the commercially pure magnesium salt of 3-nitronaphthalene-1,5-disulfonic acid by sulfonating naphthalene, nitrating the sulfonation product, and separating the pure magnesium salt of 3-nitronaphthalene-1,5-disulfonic acid, which process comprises (a) sulfonating naphthalene with liquid $SO_3$ in the presence of an inert organic solvent at temperatures between −40° and +20° C., the ratio of added $SO_3$ to added naphthalene being during the whole course of addition in the range of 2.5 to 5 mols of $SO_3$ per mol of naphthalene;

(b) adding to the reaction mixture obtained a mixture consisting of about equal parts of 100% sulfuric acid and fully reacted crude nitration mixture from nitration of a preceding nitration charge, separating from the resulting two-phase system the upper organic solvent phase by decanting, and removing from the AA-anhydride slurry the remainder of organic solvent by distillation, advantageously by flash evaporation, or, if desired, allowing it to be drawn off during subsequent nitration with simultaneous elimination of the heat of nitration, or separating it after nitration has been performed, subsequently adding to the residue the amount of nitric acid required for nitration, advantageously as mixed acid, at a temperature of between 10° C. and 60° C., and nitrating at this temperature for 1 to 6 hours;

(c) adding then firstly water and afterwards, in the absence of the inert organic solvent, at 90° to 120° C., a compound releasing magnesium ions, the amount being such that, per mol of 3-nitronaphthalene-1,5-disulfonic acid, 1.1 to 1.3 mols of magnesium ions are added, and a sulfuric acid concentration between 40 and 60 percent by weight (relative to the sulfuric acid and water) is maintained; and (d) separating the precipitated magnesium salt of 3-nitronaphthalene-1,5-disulfonic acid at a temperature of between 20° and 70° C., and subsequently optionally washing it with a maximum of 60 percent by weight of sulfuric acid and/or water.

In the process according to the invention, naphthalene and $SO_3$ are preferably dissolved separately in an inert organic solvent, particularly in an aliphatic chlorinated hydrocarbon having 1 to 3 C atoms, especially dichloromethane, and the two solutions are then combined at about −10° to −5° C., a molar ratio of added $SO_3$ to added naphthalene in the range of 2.5 to 3.6, preferably 2.8 to 3.2 being maintained during the whole course of the addition. There is formed a sulfonation product of naphthalene, which product precipitates in solid form and contains $H_2SO_4$ and optionally $SO_3$. The sulfonation product is present as a suspension in the solvent used.

This sulfonation product of naphthalene, in the following designated also as Armstrong's acid anhydride or AA-AN, is a mixture of oligomeric anhydrides of naphthalene-di- and -tri-sulfonic acids with $H_2SO_4$ and possibly $SO_3$. If the sulfonated naphthalene units present in the AA-AN are in general considered as naphthalene-sulfonic acids and sulfuric acid as $SO_3$, the AA-AN mixture can contain for example 69 to 88 percent by weight of naphthalene-di- and -tri-sulfonic acids and 31 to 12 percent by weight of $SO_3$, and contains generally, relative to the total amount of naphthalenesulfonic acids, over 65 percent by weight of naphthalene-1,5-disulfonic acids.

There is preferably used according to the invention AA-AN which, generally considered, contains 70 to 82 percent by weight of naphthalene-1,5-disulfonic acid, relative to the total amount of naphthalenesulfonic acids, for example a mixture of the composition:

75 to 80 wt.% of naphthalene-1,5-disulfonic acid,
0 to 3 wt.% of naphthalene-1,3-disulfonic acid,
5 to 15 wt.% of naphthalene-1,6-disulfonic acid,
2 to 5 wt.% of naphthalene-1,7-disulfonic acid,
0 to 5 wt.% of naphthalene-1,3,5-trisulfonic acid,
0 to 5 wt.% of naphthalene-1,3,6-trisulfonic acid,
0 to 1 wt.% of naphthalene-1,3,7-trisulfonic acid,
0 to 1 wt.% of naphthalene-1-sulfonic acid, in each case relative to the sum of all naphthalene derivatives, and calculated as free sulfonic acid.

The AA-AN can in addition contain very minute amounts of further dinaphthylsulfones and dinaphthylsulfonesulfonic acids, not more closely identified.

The particular advantage of the novel process is that it is possible with the crude reaction mixture to directly process further, without isolation of the pure sulfonation product.

The processing of the AA-AN into the form of dry substance and the storage and dosing thereof prove to be very involved operations. The handling and also filtration, drying, storage in silos and dosing of the AA-AN demand expensive equipment of a special type, since the AA-AN is highly hygroscopic, and furthermore it quickly becomes, when for example it is mechanically worked at temperatures above 30° C., a rubber-like mass that can virtually no longer be further processed. The low-temperature drying necessary would moreover consume a great amount of energy.

A way of avoiding this handling of the solid substance would appear to be the direct application of the sulfonation mixture for the subsequent nitration stage. This is however not a practical solution because with too low an amount of sulfuric acid the result is likewise a rubber-like mixture; the use of sufficient amounts of sulfuric acid of more than 15 mol per mol of AA-AN is uneconomical on a large commercial scale, and from an ecological standpoint no longer acceptable.

It has now been found that by recycling a portion of the crude nitration mixture from a previous nitration batch, it is surprisingly possible to reduce the sulfuric acid amount required in conventional processes down to 20%, and that furthermore the AA-AN is obtained as a pumpable slurry very well suited for further processing.

The acid mixture of concentrated sulfuric acid and fully reacted nitration mixture, which acid mixture is to be used in stage (b) for phase separation after the sulfonation reaction, can be varied, but the total amount of the mixture advantageously is to consist of at least 6 parts by weight, and each of the two individual components of at least 3 parts by weight per 1 part of naphthalene used in the sulfonation reaction. If the two components are added to the sulfonation mixture not as an acid mixture but as individual components in any sequence, there is formed an unstirrable mass. The use of the acid mixture is therefore of decisive importance.

A particularly preferred embodiment of stage (b) of the novel process comprises introducing the AA-AN slurry obtained after phase separation and the mixed acid either successively or simultaneously into a crude nitration mixture, and subsequently nitrating as already described. In this modification of the process, the crude nitration mixture thus obtained is divided into three portions. One portion is worked up to give 3-nitronaphthalene-1,5-disulfonic acid by dissolving the portion in water at 80° to 100° C. and isolating it as the magnesium salt; the second portion is mixed with 100% sulfuric acid in the ratio of 1:1, and the mixture is added to the sulfonation mixture to effect phase separation; and the third portion is used as crude nitration mixture for a subsequent nitration reaction according to the preferred embodiment described above.

The aforementioned removal of the final residues of solvent from the reaction system, which still remain after decanting, presents no fundamental problem. Removal of these residues can be effected optionally either before the nitration reaction by means of so-called flash evaporation (rapid evaporation) with application of a vacuum, or during nitration by distillation, utilising the heat of nitration, by virtue of which external cooling systems for cooling the reaction can be dispensed with.

Nitration in stage (b) of the process according to the invention can even be performed in the presence of the solvent present in the sulfonation product, preferably however in the absence of solvent.

The operation for separating the two-phase liquid mixture after the sulfonation reaction is performed preferably at room temperature; and separation of the residual solvent from the acid phase is advantageously effected by so-called flash evaporation at about 10° to 30° C. and 20 to 100 torr. The solvent recovered by decantation and flash distillation can be re-used directly in the sulfonation reaction. There thus occur virtually no solvent losses, a factor which renders the process extremely favourable from an ecological point of view.

Suitable inert organic solvents for the present process are in particular chlorinated hydrocarbons, for example dichloromethane, chloroform, tetrachloromethane and 1,2-dichloroethane; on account however of the need to save energy, readily boiling chlorinated hydrocarbons are of special interest, dichloromethane being preferred.

The simultaneous addition of the AA-AN slurry and the mixed acid to the residual amount of nitration mixture, which is the preferred procedure for nitration, renders possible on a commercial scale, right from the commencement, the removal of the high heat of nitration and the maintenance of the temperature limits of 10° to 60° C., preferably 35° to 45° C., which are required according to the invention. There would otherwise be necessary a special external cooling circulation system. The said mode of procedure is also advantageous in that dosage variations have no disadvantageous effect, and that the safety of the process, even in the case of extensive proportioning errors or with the occurrence of other faults, for example a cooling failure, is always ensured.

The dosing rate is preferably adjusted to approximately correspond to the nitration rate. The dosing time is preferably between 1 and 3 hours. After completion of dosing, the reaction mixture is allowed to fully react in the course of 0.5 to 3 hours at 10° to 60° C. Preferably, the after-reaction time is 1 to 2 hours at 35° to 45° C.

There are advantageously used for nitrating 1 to 1.5 mols of conc. nitric acid in the form of mixed acid per mol of naphthalene used. The mixed acid preferably consists of concentrated sulfuric acid which contains 0.8 to 1.2 mols of $SO_3$ per mol of nitric acid.

The stage (c) of the present process performs in particular a partial purification function, and provides advantages relating to processing in that the product is obtained in the form of crystals that are easy to isolate.

The bulk of undesired by-products is constituted by 3-nitronaphthalene-1,6-disulfonic acid. Like nitro-Armstrong acid (3-nitronaphthalene-1,5-disulfonic acid), this compound forms a difficultly soluble magnesium salt. In further processing of nitro-AA to C acid, it is however necessary to remove this by-product beforehand since C acid is very readily soluble and is normally obtained by concentrating the reaction solution by evaporation. Surprisingly, it is possible, by crystallisation at 90°–120° C. and filtration of the nitration mixture in the form of the magnesium salts at 60° C., to largely maintain the by-products including 3-nitronaphthalene-1,6-disulfonic acid in solution, and to separate them with the mother liquor, so that the practically pure dimagnesium salt of nitro-Armstrong's acid remains behind as the filter residue. This is of particular importance because the isolation of the magnesium salt of nitro-AA by precipitation, filtration and washing by processes known from the literature creates considerable difficulties and leads to high processing costs; furthermore, it is scarcely possible to obtain the salt in a sufficiently pure form because there is formed in processing a very fine crystal sludge as a thixotropic phase, which is extremely difficult to filter and wash, the result being that the filter cake has a high residual moisture content and is heavily contaminated. The only method which has hitherto proved commercially practicable is the laborious washing of the filter cake with aqueous sodium chloride solution, a procedure which results in a contamination of the magnesium salt of nitro-AA with sodium chloride.

The filtration of the crystals of the Mg salt of nitro-AA presents a real engineering problem, and at the same time an ecological problem since large amounts of diluted sulfuric acid and subsequently of washing water for afterwashing are required.

Crystallisation at elevated temperatures according to stage (c) of the invention has the surprising results
(a) that the Mg salt of nitro-AA is obtained in the form of readily filterable crystal-grain distributions, and
(b) that the yield of the pure Mg salt of nitro-AA is increased.

The reaction mixture from the nitration of 1,5-naphthalenedisulfonic acid contains sulfuric acid from the mixed acid nitration stage. This acid is diluted and serves as reaction medium in the crystallisation process. By virtue of the requirement of water for filtration and washing of the Mg salt of nitro-AA, and the necessary recycling of the washing water, it is advantageous in the crystallisation process to have a minimum dilution of the sulfuric acid of 50%, and a temperature of between 90° and 120° C. The concentration of sulfuric acid can however vary between 40 and 60%.

Suitable magnesium-containing precipitants are magnesium salts, such as magnesium sulfate or magnesium carbonate, and magnesium oxide. The preferred precipitant is however magnesium sulfate in the form of bitter salt (magnesium sulfate heptahydrate). These compounds can be used for example dissolved in water or in admixture with water. The magnesium salt (bitter salt solution) is used in amounts of 110 to 130 mol.%, relative to the content of nitro-Armstrong's acid. The optimum amount is 120 to 122 mol.%.

The most advantageous crystallisation temperature is between 95° and 100° C.

The reaction stages (c) and (d) are preferably carried out as follows:

The water required for dilution of the sulfuric acid is placed into a container with stirrer. The nitration solution of 1,5-naphthalenedisulfonic acid is then introduced at such a rate that, with only slight cooling, the temperature of the solution remains at about 100° C. This is followed by crystallisation of the Mg salt of nitro-AA by addition of a compound releasing magnesium ions, preferably an aqueous bitter salt solution. Preferably, 1.20 to 1.22 mols of bitter salt solution are used per mol of nitronaphthalenesulfonic acid, and the total amount is added within about 60 minutes. The concentration in the aqueous solution is as a rule about 20 to 25% of $MgSO_4$. After crystallisation, stirring is maintained for about 60 minutes at about 90° to 100° C.; the temperature is then lowered in the course of about 60 minutes to about 20° to 70° C., preferably 50° to 60° C., and filtration is performed. The suction-filter residue is subsequently washed with water.

In order to remove the slight amount of residual sulfuric acid from the moist magnesium salt of nitro-AA, a washing, if desired, with up to 3 kg of water per mol of magnesium salt suffices. In contrast to washing in the processes known hitherto, this washing operation is technically simple and easy to carry out. The filter cake thus obtained can be used directly in a subsequent reduction stage.

The Mg salt of nitro-AA obtained by this crystallisation process has a particle size distribution of between 30 and 150 $\mu$m. The salt can be easily filtered and washed, in consequence of which only a very small amount of washing liquid is involved in the operation. The purity of the product increases quite considerably. It was possible to reduce the amount of contaminating isomeric by-products to below 2%.

A continuous crystallisation variant can comprise for example continuously spraying through nozzles the two solutions of nitro-AA reaction mixture and bitter salt solution into each other, as a result of which the synchronous dosing occurring—optionally in the presence of inoculation nuclii—produces an optimum precipitation result.

The advantages of stage (c) are that the Mg salt of nitro-AA obtained by the novel crystallisation process is readily filtered and washed, in consequence of which only a very small amount of washing liquid accumulates; the purity of the product increases very considerably; the contaminating isomeric by-products can be reduced to below 2%; and the product can be washed with water. In the case of prior known processes, it was necessary to wash with 45% sulfuric acid since it was not possible to wash the occurring fine crystals of between 5 and 15$\mu$ with water. The sulfuric acid for washing then contaminated the waste-water. It was previously necessary to operate with filter presses, whereas it is now possible to use normal filters.

It is stated in U.S. Pat. No. 2,191,820 that nitration has to be performed under anhydrous conditions in order to suppress the formation of 1-nitronaphtalene-4,8-disulfonic acid. Since naphthalene-1,5-disulfonic acid crystallises as tetrahydrate (see Ullmann's Enzykopädie der technischen Chemie, 3rd Edition, Vol. 12, p.595), there has to be used in the process according to U.S. Pat. No. 2,191,820 large amounts of oleum in order to render possible, by binding the crystal water, nitration in an anhydrous medium. In the process according to the present invention, naphthalene-1,5-disulfonic acid is used in the form of the anhydrous Armstrong's acid anhydride, and therefore requires considerably less oleum or $SO_3$ in order to keep the nitration mixture anhydrous.

It is to be considered decidedly surprising that it is possible under the conditions according to the invention to precipitate the magnesium salt of the nitro-AA in a form which is readily filterable and washable, and which enables an excellent separation of the isomers to be effected. It is known from the U.S. Pat. No. 1,756,537 (1930) that it is possible to isolate the magnesium salt of nitro-AA from nitration mixtures, which occur with the nitration of naphthalene-1,5-disulfonic acid or mixtures thereof with naphthalene-1,6-disulfonic acid, by addition of the magnesium salt at temperatures of between 0° and 100° C., and crystallisation at 0° to 10° C. In the subsequently published Russian Inventor Certificate No. 154,261 (1963), it is however described how, contrary to the solution found in the present invention, the magnesium salt of nitro-AA occurs in the form of small crystals which are difficult to filter and to wash, and how the separation therefrom of isomers is rendered difficult. It is therefore suggested in the Russian Inventor Certificate No. 154,261 that the separation of nitro-Armstrong's acid from nitration mixtures be effected in the form of the ammonium salt, because in that case coarse, readily filterable and washable crystals are obtained.

The yields attainable in the process according to the invention are high. Relative to the naphthalene used in the sulfonation reaction, a yield of isolated magnesium salt of nitro-AA of about 70% can be obtained. As a result of the concentrated procedure, the space-time yield is also very favourable. The purity of the magnesium salt of nitro-AA produced according to the invention is high, although no pure naphthalene-1,5-disulfonic acid is used in nitration and although, as is known, a number of undesired by-products are formed during nitration (see U.S. Pat. No. 1,756,537). The consumption of auxiliaries, such as sulfuric acid and oleum, is greatly reduced compared with the consumption thereof in known processes. There accumulate therefore after isolation of the magnesium salt of nitro-AA appreciably smaller amounts of diluted acid. A further advantage is that there can be obtained in the process according to the invention a nitro-AA which is virtually free from sulfuric acid and salt, and hence, on its further processing to C acid, also a C acid having a low salt content.

2-Nitronaphthalene-4,8-disulfonic acid or the magnesium salt thereof is an important intermediate compound for producing the corresponding 2-naphthylamine-4,8-disulfonic acid (C acid). C Acid is used as diazotisation component for cotton dyes, and as intermediate product for producing 2-naphthol-4,6-disulfonic acid (see Ullmann's Enzyklopädie der technischen Chemie, 3rd Edition, Vol. 12, page 629).

The following Examples further illustrate the novel process.

EXAMPLE 1

(Stage a)

192.3 g of naphthalene (1.5 mols) are dissolved in 961.0 g of dichloromethane, and at the same time 360.3 g of liquid $SO_3$ are dissolved in 1540 g of dichloromethane. The two solutions are cooled to $-10°$ C., and simultaneously introduced into dichloromethane (600 g) likewise cooled to $-10°$ C., by which procedure the two mixtures are added in the same interval of time. The reaction mixture is held, by evaporative cooling at 70 to 80 torr, at a temperature of between $-5°$ and $-10°$ C. The distillate from evaporative cooling (total 1209 g) is further utilised for dissolving $SO_3$. The sulfonation reaction is finished after about 1 to 2 hours. There is obtained a suspension of the sulfonation-reaction mixture which, considered generally, has the following composition:

55.6 wt.% of naphthalene-1,5-disulfonic acid,
0.2 wt.% of naphthalene-1,3-disulfonic acid,
5.9 wt.% of naphthalene-1,6-disulfonic acid,
2.3 wt.% of naphthalene-1,7-disulfonic acid,
2.7 wt.% of naphthalene-1,3,5-trisulfonic acid,
5.9 wt.% of naphthalene-1,3,6-trisulfonic acid,
0.8 wt.% of naphthalene-1,3,7-trisulfonic acid, and 26.0 wt.% of $SO_3$.

(Stage b)

In a separate flask, 800 g of crude nitration-reaction mixture (recycled from previous nitration batch) and 732 g of $H_2SO_4$ (100%) are mixed together. The mixture from the separate flask is now added at 20° C. to the suspension from the sulfonation reaction (1.17 mols of naphthalene-1,5-disulfonic acid and 0.33 mol of isomeric di- and trisulfonic acid), and the whole is slowly stirred until the dichloromethane clearly separates in the upper layer, whereupon it can be filtered off with suction (decanted). The dichloromethane (about 1400 g) thus obtained is recycled, without further processing, into the sulfonation reaction. The residual 414 g of dichloromethane are distilled off, at 10° to 30° C. and 20 torr, by a so-called flash evaporation, and can likewise be re-utilised. At 20 torr, the temperature of the distillation residue is maintained at 20° C., and at this temperature it is fed into the subsequent nitration stage.

Nitration is performed by the simultaneous addition of 312 g of mixed acid of the following composition:
33.1 wt.% of $HNO_3$,
26.9 wt.% of $H_2SO_4$,
40.0 wt.% of $SO_3$, and 2083 g of distillation-residue slurry at 30° to 40° C. to 2400 g (residual amount) of the nitration mixture from a previous batch. The mixture is then allowed to fully react with continual stirring at 40° C., which in all takes about 4 hours.

A portion (800 g, about 1/6) of the crude reaction mixture obtained is recycled for use in the two-phase separation stage already described.

(Stage c)

A second portion (about 2/6) is processed as follows: 1594 g of the nitration mixture are added in the course of 30 minutes, with vigorous stirring, to 1123 g of cold water in a corrosion-resistant reaction vessel with a double-wall jacket, the temperature being held at 100° C. by slight cooling, in the course of which the reaction mixture goes completely into solution. After completion of the addition, the selective precipitation of the Mg salt of nitro-Armstrong's acid is effected by adding 654 g of an aqueous bitter salt solution ($MgSO_4$-content $= 158.0$ g) during 60 minutes.

(Stage d)

390 g of washing liquor from a previous precipitation stage are subsequently added within 5 minutes. The suspension is slowly stirred at 95° C. for 60 minutes; it is then cooled to 60° C. and stirred for a further 60 minutes, whereupon filtration of the coarse-crystalline suspension is performed. The filter cake is afterwards pressed out and the mother liquor filtered off with suction; the product is then washed with 300 g of cold water and dried with suction. The mother liquor and washing liquor are collected separately since only the washing liquor is recycled.

About 590 g of moist dimagnesium salt of 3-nitronaphthalene-1,5-disulfonic acid are obtained, which corresponds to 366 g of 100% dry substance (about 70% yield, relative to the naphthalene used). The proportion of isomeric by-products in the product is lower than 1.5%.

A third portion, that is to say, the remainder of the crude nitration-reaction mixture (2400 g, about 3/6), is re-used, particularly when carrying out the process on a commercial scale, as material for a further nitration batch.

When the mixed acid and the distillation residue are added in the nitration reaction not simultaneously but one after the other, so that in each case a small portion of AA-AN slurry is added followed by the required amount of mixed acid, the final product is obtained in the same yield and quality.

EXAMPLE 2

The procedure is carried out as in Example 1 except that the dichloromethane is not removed from the sulfonation product of naphthalene, and the product is used in the form of a 30 wt.% suspension in dichloromethane in the subsequent nitration reaction. There is obtained a yield of magnesium salt of 3-nitronaphthalene-1,5-disulfonic acid of 67% relative to naphthalene and of 87% relative to naphthalene-1,5-disulfonic acid, in the form of the employed sulfonation product. The dichloromethane is slowly removed by distillation during the addition of the nitration mixture.

What is claimed is:

1. A process for producing the magnesium salt of 3-nitronaphthalene-1,5-disulfonic acid by sulfonating naphthalene, nitrating the sulfonation product, and separating the pure magnesium salt of 3-nitronaphthalene- 1,5-disulfonic acid, which process comprises the steps of:

(a) sulfonating naphthalene wth liquid $SO_3$ in the presence of an inert organic solvent at temperatures between $-40°$ and $+20°$ C., the ratio of added $SO_3$ to added naphthalene being during the whole course of addition in the range of 2.5 to 5.0 mols of $SO_3$ per mol of naphthalene;

(b) adding to the reaction mixture obtained a mixture consisting of about equal parts of 100% sulfuric acid and fully reacted crude nitration mixture obtained at the end of step (b), separating from the resulting two-phase system the upper organic solvent phase by decanting, and removing from the Armstrong's acid anhydride slurry the remainder of organic solvent by distillation, subsequently adding to the residue the amount of nitric acid required for nitration, in admixture with sulfuric acid and $SO_3$, at a temperature of between 10° and 60° C., and nitrating at this temperature for 1 to 6 hours;

(c) adding then firstly water and afterwards, in the absence of the inert organic solvent, at 90° to 120° C., a compound releasing magnesium ions, the amount being such that per mol of 3-nitronaphthalene-1,5-disulfonic acid, 1.1 to 1.3 mols of magnesium ions are added, and a sulfuric acid concentration of between 40 and 60 percent by weight (relative to the sulfuric acid and water) is maintained; and (d) separating the crystallised magnesium salt of 3-nitronaphthalene-1,5-disulfonic acid at a temperature of between 20° and 70° C., and subsequently optionally washing it with a maximum of 60 percent by weight of sulfuric acid and/or water.

2. A process according to claim 1, wherein the acid mixture of concentrated sulfuric acid and fully reacted crude nitration mixture obtained at the end of step (b), which mixture is to be used for phase separation after the sulfonation reaction, consists of at least 6 parts by weight, and each of the two individual components of at least 3 parts by weight, per 1 part of naphthalene used in the sulfonation reaction.

3. A process according to claim 1, wherein there are used for nitration 1 to 1.5 mols of nitric acid, in admixture with $SO_3$ and sulfuric acid, per mol of naphthalene.

4. A process according to claim 1, wherein acid mixture used for nitration contains 0.8 to 1.2 mols of $SO_3$ per mol of nitric acid.

5. A process according to claim 1, wherein phase separation of solvent and Armstrong's acid anhydride slurry is performed continuously.

6. A process according to claim 1, wherein the 3-nitronaphthalene-1,5-disulfonic acid formed as product crystallises out as magnesium salt after previous dissolving of the reaction mixture in water at 90° to 120° C.

7. A process according to claim 6, wherein the crystallisation of magnesium salt is performed by means of magnesium salt solutions or suspensions at a temperature of between 95° and 100° C., and magnesium salt is used in amounts of 1.1 to 1.3 mols per mol of nitro-Armstrong's acid.

8. A process according to claim 1, wherein the filtered-off magnesium salt of nitro-Armstrongs's acid is washed only with water without previous washing with sulfuric acid.

9. A process according to claim 1, wherein magnesium sulfate is used for the precipitation of magnesium salt.

10. A process according to claim 1, wherein from the Armstrong's acid anhydride slurry in step (b) the remainder of organic solvent is removed by flash evaporation.

11. A sulfonation process according to claim 1, wherein $SO_3$ and naphthalene are each dissolved separately in an inert organic solvent and the two solutions are then combined at about $-10°$ to $-5°$ C., a molar ratio of added $SO_3$ to added naphthalene in the range of 2.5 to 3.6 being maintained during the whole course of the addition.

12. A sulfonation process according to claim 11, wherein as an inert organic solvent an aliphatic chlorinated hydrocarbon having 1 to 3 carbon atoms is used.

13. An sulfonation process according to claim 11, wherein as an inert organic solvent dichloromethane is used.

14. A sulfonation process according to claim 11, wherein the molar ratio of added $SO_3$ to added naphthalene is in the range of 2.8 to 3.2.

15. A process for producing the magnesium salt of 3-nitro-naphthalene-1,5-disulfonic acid by sulfonating naphthalene, nitrating the sulfonation product, and separating the pure magnesium salt of 3-nitro-naphthalene-1,5-disulfonic acid, which process comprises the steps of (a) sulfonating naphthalene with liquid $SO_3$ in the presence of an inert organic solvent at temperatures between $-40°$ and $+20°$ C., the ratio of added $SO_3$ to added naphthalene being during the whole course of addition in the range of 2.5 to 5.0 mols of $SO_3$ per mol of naphthalene;

(b) adding to the reaction mixture obtained a mixture consiting of about equal parts of 100% sulfuric acid and fully reacted crude nitration mixture obtained at the end of step (b), separating from the resulting two-phase system the upper organic solvent phase by decanting and adding the lower phase which is the Armonstrong's acid anhydride slurry and nitric acid, either simultaneously or one after the other, to a second portion of crude nitration mixture obtained at the end of step (b) and performing the nitration at a a temperature of between 10° and 60° C., for 1 to 6 hours (c) preparing the magnesium salt of 3-nitronaphthalene-1,5-disulfonic acid adding then firstly water and afterwards, in the absence of the inert organic solvent, at 90° to 120° C., a compound releasing magnesium ions, the amount being such that per mol of 3-nitronaphthalene-1,5-disulfonic acid, 1.1 to 1.3 mols of magnesium ions are added, and a sulfuric acid concentration of between 40 and 60 percent by weight (relative to the sulfuric acid and water) is maintained; and (d) separating the crystallised magnesium salt of nitronapthalene-1,5-disulfonic acid at a temperature of between 20° and 70° C., and subsequently optionally washing it with a maximum of 60 percent by weight of sulfuric acid and/or water.

16. A process according to claim 15, wherein the two portions of crude nitration mixture used are obtained by dividing the crude nitration mixture at the end of step (b) into three portions, of which one portion is mixed with 100% sulfuric acid in the ratio of 1:1 and the mixture is added to the sulfonation mixture for the purpose of phase separation; the second portion is used as material for the subsequent nitration reaction; and the third portion is processed to give the magnesium salt of nitro-Armstrong's acid.

* * * * *